United States Patent [19]
Scholes et al.

[11] Patent Number: 4,569,795
[45] Date of Patent: Feb. 11, 1986

[54] ARYLSULPHONYL AZETIDINE COMPOUNDS, THEIR PREPARATION AND THEIR USE AS INTERMEDIATES

[75] Inventors: Gary Scholes; Robert van Helden, both of Amsterdam, Netherlands

[73] Assignee: Shell Oil Company, Houston, Tex.

[21] Appl. No.: 569,419

[22] Filed: Jan. 9, 1984

[30] Foreign Application Priority Data

Jan. 13, 1983 [GB] United Kingdom ............... 8300860

[51] Int. Cl.⁴ ............... C07D 205/04; C07D 491/113; A01N 43/44
[52] U.S. Cl. ................ 260/239 A; 549/334; 71/88
[58] Field of Search ............... 260/239 AR

[56] References Cited

FOREIGN PATENT DOCUMENTS 29265 5/1981 European Pat. Off. .

OTHER PUBLICATIONS

Anderson et al., Chem. Abstracts, vol. 81, (1974), p. 398, abstract 135842u.
March, ed., Advanced Organic Chemistry, 2nd ed., McGraw-Hill, N.Y., (1977), p. 1107.

Primary Examiner—Donald G. Daus
Assistant Examiner—William A. Teoli, Jr.

[57] ABSTRACT

Azetidine compounds of the general formula I

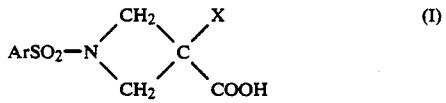

wherein Ar represents a para-tolyl group and X represents a hydrogen atom, a carboxyl group or a hydroxymethyl group; their preparation from pentaerythritol via compounds of formula

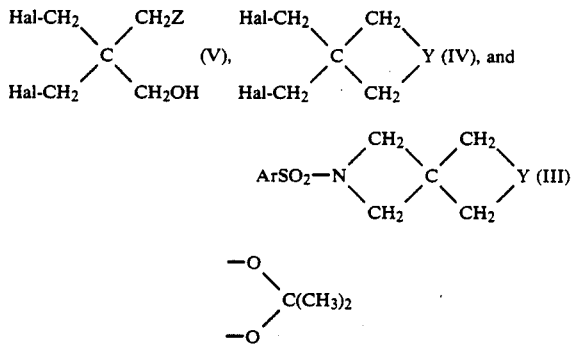

or two hydroxyl groups and Z represents Hal or OH, together with their use as intermediates in the preparation of 3-carboxyazetidine; also the compounds of formula

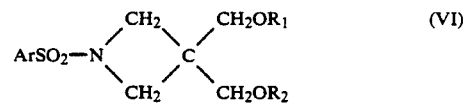

wherein $R_1$ and $R_2$ both represent hydrogen, or together represent

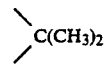

The compounds are intermediates for a known chemical hybridizing agent.

1 Claim, No Drawings

ARYLSULPHONYL AZETIDINE COMPOUNDS, THEIR PREPARATION AND THEIR USE AS INTERMEDIATES

This application relates to arylsulphonyl azetidine compounds, which are useful as intermediates in the preparation of biologically active azetidine compounds, together with the preparation of such intermediates.

It is known from European patent application No. 29265 that 3-carboxyazetidine and related compounds are chemical hybridising agents, their mode of action presumably being based on their ability to produce male sterility in plants. That application also describes a process for their preparation, starting from 3-cyano-1-diphenylmethylazetidine, which may be prepared by methods known per se. Although the process described works well, it is not ideally suited for large scale preparations, since the bulky diphenylmethyl group on the nitrogen atom is removed only in the last of a series of steps, which means that in all but the last step large equipment is needed. Moreover, the apparent starting compound diphenylmethylamine is relatively expensive.

It is the object of the invention therefore to provide an improved process for the preparation of a 3-carboxyazetidine compound, which is achieved firstly by the provision of novel intermediates and secondly by the provision of a process for their preparation, starting from readily available compounds.

Accordingly the invention relates to 1-arylsulphonyl-3-carboxy azetidine compounds of the general formula I:

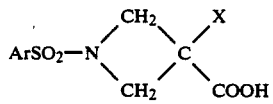
(I)

wherein Ar represents a para-tolyl group, and X represents a hydrogen atom, a carboxyl group or a hydroxymethyl group.

The invention also relates to a process for the preparation of a compound of formula I which comprises oxidising a compound of the general formula II

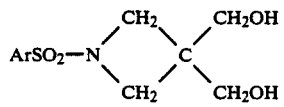
(II)

followed, when the desired product is that wherein X is a hydrogen atom, by decarboxylation. The oxidation may conveniently be carried out by contact with gaseous oxygen in the presence of a catalyst, such as platinum or palladium on carbon. The extent of the oxidation, i.e. whether the product obtained is that wherein X represents hydroxymethyl or carboxyl is influenced by the temperature, pH and duration of the oxidation process. The decarboxylation reaction, i.e. conversion of a product wherein X represents carboxyl to one wherein X represents hydrogen, is suitably carried out by heating the dicarboxyl compound for an adequate period of time, an operation which may, where convenient, be integrated into the oxidation process whereby the starting material of formula II may be directly oxidised and decarboxylated to the end product of formula I wherein X represents hydrogen.

The compound of formula II may suitably be prepared by (i) reacting p-tosylamide with a cyclic ether of formula III.

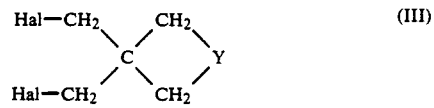
(III)

wherein each Hal represents a chlorine, bromine or iodine atom and Y represents an oxygen atom or the group

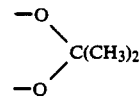

in the presence of a dehydrohalogenating agent, such as a strong base, thereby forming an azetidine derivative of formula IV

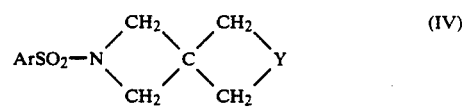
(IV)

and (ii) reacting the azetidine derivative of formula IV with an aqueous solution of strong acid.

The reaction conditions for step (i) are similar to those employed in analogous reactions. Preferably more severe conditions are applied to achieve the necessary dehydrohalogenation when the halo atoms to be removed are chlorine. Thus whereas sodium ethanolate in ethanol at 80° C. to 100° C. suffices when the halo atoms are bromine, a base like potassium tert.butoxide in an aprotic polar solvent like dimethyl sulphoxide or dimethyl formamide, at 120° C. to 150° C. is preferably applied whem the halo atoms are chlorine.

In step (ii) the product of step (i) is converted into the compound of formula II by the action of a diluted strong acid, preferably an inorganic acid and especially $H_2SO_4$. Refluxing for 1-5 hours will usually result in a quantitative reaction. In fact, the oxygen containing ring is broken up and a propanediol moiety formed. When using a halo acid such as (diluted) HCl, side-reactions may occur, e.g. substitution of hydroxy groups by halo atoms or even opening of the nitrogen containing ring. These side-reaction products can be converted into the desired product by a subsequent reaction with base, e.g. diluted NaOH.

The compounds of formula III may suitably be prepared by reacting pentaerythritol with hydrogen chloride, bromide or iodide to yield a product of formula:

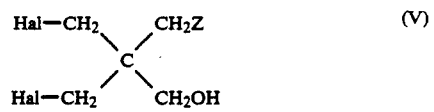
(V)

wherein Z represents Hal or hydroxy, followed by (i) when Z represents Hal, reaction with a base to effect dehydrohalogenation to yield the oxetane of formula III above wherein Y represents an oxygen atom or (ii) when Z represents hydroxy, reaction with acetone to form the ketal of formula III above wherein Y represents

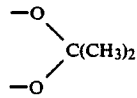

It will be readily apparent that pentaerythritol is an inexpensive and readily available commodity product and thus represents a very convenient starting material.

The first stage, reacting with HCl, HBr or HI, essentially is a substitution of hydroxy groups by halide atoms. HCl is a slightly less preferred reagent, since it appears that subsequent steps proceed less quickly with chlorinated compounds than with brominated etc. compounds. The reaction may be performed with pure, gaseous HCl, HBr or HI, or with previously prepared solutions thereof. However, these solutions are not restricted to aqueous solutions, and they also include solutions of related compounds in which HCl, HBr or HI may be formed in situ. Thus particularly preferred reactant/solvent combinations are for example: aqueous HBr with acetic acid, and thionyl chloride with pyridine.

According to the reaction conditions, substitution by two or three halo atoms may be effected. Bis-halo substitution may be carried out using HCl, HBr or HI gas according to procedures known per se, e.g. as described in U.S. Pat. No. 3,932,541. The bis-chlorosubstituted product (dichlorohydrin) is also available commercially. The tris-halo substitution may be effected by methods known for analogous compounds e.g. by boiling pentaerythritol, acetic acid and aqueous HBr and adding sulphuric acid, followed by working up the reaction products with a chloroform extraction, or by using SOCl$_2$ in pyridine.

In the second step (i) the tris-halo substituted pentaerythritol, e.g. C(CH$_2$Cl)$_3$(CH$_2$OH), is converted into a bis-halomethyloxetane by the dehydrohalogenating action of a suitable base. Suitable bases include, for example, sodium or potassium ethanolate or other alcoholates, or conveniently sodium or potassium hydroxide, dissolved in a polar solvent, e.g. ethanol.

In the second step (ii) the bis-halo substituted pentaerythritol, e.g. C(CH$_2$Br)$_2$(CH$_2$OH)$_2$, is cyclised by derivatizing the two hydroxy groups by preparing a formal, acetal or ketal using formaldehyde, a higher aldehyde or a ketone. Preferably acetone is used to prepare a cyclic ketal. Conveniently a catalytic amount of acid is present when reacting with an aldehyde or ketone.

The compounds of formula II, and those of formula IV wherein Y represents the grouping

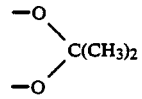

i.e. azetidine derivatives of the general formula VI

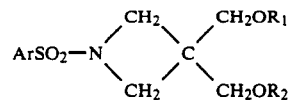

wherein R$_1$ and R$_2$ both represent hydrogen or R$_1$ and R$_2$ together represent the group

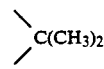

are novel and as such are included within the scope of this invention.

The invention also relates to the use of the arylsulphonyl azetidines of formula I as defined above as intermediates for the preparation of 3-carboxyazetidine. Such a preparation is achieved by removal of the (protective) ArSO$_2$ group, which may be carried out by methods known in the art for the operation. Such methods include, e.g. hydrogenating using a suitable catalyst/solvent system, e.g. acetic acid, or, preferably, employing sodium in liquid ammonia. If desired, the 3-carboxyazetidine may be further substituted. The substituents may be introduced both during the foregoing series of reaction steps, or thereafter, and they could even be introduced into the 3-carboxyazetidine itself.

The invention will now be illustrated further by the following Examples. NMR values are chemical shifts in ppm, relative to tetramethylsilane.

EXAMPLE 1

Preparation of 3,3-bishydroxymethyl-1-tosylazetidine via the acetone-ketal (i) Dibromohydrin (10 g; 38 mmol) was mixed with 5 ml acetone, 0.1 g of p-toluenesulphonic acid and 150 ml of benzene and heated under reflux with stirring, while water was removed continuously by means of a Dean-Stark trap. When the separation of water ceased, after about 2 h, the solvent was evaporated. The remaining solid (11.5 g) consisted of 5,5-bisbromomethyl-2,2-dimethyl-1,3-dioxane.

(ii) The compound prepared in step (i) (11.5 g, 38 mmol) and paratoluenesulphonamide (6.5 g, 38 mmol) were mixed with 4.3 g potassium tert.butoxide in 150 ml dimethylformamide. The mixture was heated with stirring, to 100° C. for about 5 hours. Then the mixture was cooled and evaporated in order to remove the solvent. The residue of this was taken up in 8% aqueous NaOH; the solids were filtered off and washed with diethyl ether. After recrystallisation from CHCl$_3$, a white crystalline material (10.1 g) was obtained, consisting of pure 7,7-dimethyl-2-tosyl-6,8-dioxa-2-azaspiro[3,5]nonane. This is the acetone-ketal of the title compound. The NMR spectrum in CDCl$_3$ was as follows: 1.4(s,6H), 2.5(s,3H), 3.6(s,4H), 3.65(s,4H), 7.6(m, 4H).

(iii) The material obtained in (ii) was taken up in 100 ml 6.7% aqueous H$_2$SO$_4$ and stirred for 2 hours at 100° C. Then the mixture was neutralised with NaHCO$_3$ and extracted with CHCl$_3$. The residue was recrystallised from ethanol, yielding 83 g of colourless crystals, melting point 97°–99° C., being pure 3,3-bishydroxy-methyl-1-tosylazetidine. The NMR spectrum in CD$_3$OD was as follows: 2.5(s,3H), 3.4(s,4H), 3.5(s,4H), 4.8(s,2H), 7.6(m,4H).

EXAMPLE 2

Example 1 was repeated using dichlorohydrin instead of dibromohydrin, and the same reaction conditions, except that in step (ii) the reaction temperature was 150° C. The same product was obtained, though at somewhat lower yield.

EXAMPLE 3

The last step of Examples (1) and (2) was carried out using dilute (10%) hydrochloric acid. Stirring the ketal of step (ii) at room temperature for 48 hours resulted in a large proportion of a ring opened product being formed (3-chloro-2,2-bishydroxymethyl-propane p.toluenesulphonamide). Ring closure to the desired compound was achieved by refluxing 2½ hours in 10% aqueous NaOH.

EXAMPLE 4

Preparation of 3,3-bishydroxymethyl-1-tosylazetidine via the oxetane (i) A mixture of 72.0 g 90% pure pentaerythritol (529 mmol), 250 ml 47% HBr and 50 ml acetic acid was boiled for 18 hours, after which the solvent was evaporated. The residue plus 250 ml 47% HBr and 125 ml 96% sulphuric acid was boiled for another 8 hours. After cooling, the mixture was extracted with $3 \times 100$ ml $CHCl_3$; the chloroform layers were washed with $2 \times 100$ ml $H_2O$ and dried over anhydrous $K_2CO_3$. Filtration and evaporation of the solvent gave 128.6 g of a dark-brown viscous residue, which was distilled, yielding eventually 112.0 g of a colourless crystalline material and 4.4 g of a colourless oil. Analysis showed both the oil and the crystals to contain 2,2-bisbromomethyl-3-bromopropanol and the acetate thereof.

(ii) The 2,2-bisbromomethyl-3-bromopropanol and its acetate prepared in step (i) (55.4 g; 128 and 30 mmol respectively) were mixed with 10.0 g aqueous 85% KOH and 150 ml ethanol and refluxed for 1 hour. White solids were filtered off and the filtrate was evaporated. The residue of this evaporation was boiled with 2.5 g aqueous 25% KOH and 120 ml ethanol for 1½ hour. Again the white solids were filtered off, the filtrate evaporated and the residue boiled with the same quantities of KOH and ethanol for the same time. GLC analysis now showed that conversion was complete. The residue was taken up in 300 ml diethyl ether, washed with 100 ml water and dried over $MgSO_4$. After filtration and evaporation of the solvent, 34.0 g of a colourless liquid was obtained containing 3,3-bisbromomethyloxetane.

(iii) To a solution of 70% of Na in 200 ml ethanol 48.8 g p.toluenesulphonamide (285 mmol) in 400 ml ethanol was added: a white solid material formed which was easily stirred in the liquid. After addition of 68.8 g 3,3-bisbromomethyloxetane (241 mmol) and another 7.0 g Na in 200 ml ethanol the clear solution was stirred at the reflux temperature of 22 hours. After cooling a white solid was filtered off and the filtrate was evaporated. The residue was taken up in 300 ml 8% aqueous NaOH, the solids were filtered off and washed with 200 ml diethyl ether, after which they were recrystallised with 100 ml chloroform, yielding 43.3 g white crystalline material, being pure 6-tosyl-2-oxa-6-azaspiro[3.3]heptane, melting point 143°–145° C.

(iv) The spiro-compound prepared in (iii) (13.8 g, 55 mmol) was taken up in 280 ml water, and 0.4 ml 96% sulphuric acid was slowly added thereto. The heterogeneous reaction mixture was boiled for three hours, becoming completely clear and colourless after about two hours. The solution was cooled, neutralised with solid $NaHCO_3$ and the water was evaporated. The residue was taken up in ethanol, filtered and the ethanol was evaporated again, resulting in 14.9 g of colourless crystalline material, being pure (according to NMR and GLC) 3,3-bishydroxymethyl-1-tosylazetidine.

EXAMPLE 5

Example 4 was repeated using HCl instead of HBr in step (i). Thereafter the reaction conditions were essentially similar, and the same product was obtained.

EXAMPLE 6

Step (ii) of Example 4 was repeated using NaOEt as base instead of KOH, the actual procedure being as follows.

To 4.0 g Na in 100 ml ethanol 56.1 g of the product of step (i) (239 mmol alcohol and 31 mmol acetate) was added and the mixture was boiled for one hour. Another 1.0 g Na in 40 ml ethanol was added and the mixture was refluxed for an hour again. GLC analysis now showed that conversion was complete and the white solids that were filtered off, were worked up in the way of Example 4, yielding 35.2 g of a colourless liquid containing 3,3-bisbromomethyl-oxetane. The reaction rate was higher than in Example 4, but more by-products were formed.

EXAMPLE 7

(A) Step (iii) of Example 4 was repeated using powdered sodium hydroxide in place of sodium. To p-toluenesulphonamide (2.1 g) dissolved in dimethylsulfoxide (20 ml) was added powdered sodium hydroxide (1 g) and stirred ½ h at 25° C. when a milky solution was obtained. 3,3-bisbromomethyloxetane (3.0 g) in dimethylsulphoxide (5 ml) was then added in one portion and the mixture stirred 15 h at 25° C. Pouring into water caused precipitation of a white solid which was filtered off, washed with water and dried, to give the same azaspiroheptane as obtained in Example 4(iii).

(B) Step (iii) of Example 4 was repeated using sodium hydroxide and a phase transfer catalyst in place of sodium. 3,3-bisbromomethyloxetane (10 g, 0.041 mol) in toluene (10 ml) was added dropwise with stirring to a mixture of p-toluenesulphonamide (17 g, 0.041 mol), tetrabutylammonium hydrogensulphate (1.4 g, 0.004 mol), toluene (50 ml) and 50% NaOH (50 ml) at 60° C. After the addition was completed, the mixture was heated 3 h at 80° C. when most of the solids dissolved. Analysis (glc) showed complete disappearance of oxetane. The reaction mixture was cooled and diluted with water when a solid formed between the organic and the aqueous phases. This solid was filtered off. The toluene layer was separated and the aqueous layer extracted twice with $CH_2Cl_2$. The combined toluene and $CH_2Cl_2$ layers were dried and evaporated under reduced pressure to leave a white solid which was combined with the solid filtered off. Recrystallisation from IPA/EtOH gave the same azaspiroheptane as obtained in Example 4(iii).

EXAMPLE 8

(A) Step (ii) of Example 1 was repeated using powdered sodium hydroxide in dimethyl sulphoxide in place of potassium tert.butoxide.

A mixture consisting of the dioxane obtained in Example 1(i) (5 g, 0.166 mol) p-toluenesulphonamide (2.8 g, 0.0166 mol) and powdered sodium hydroxide (1.4 g, 0.0332 mol) dissolved in dimethyl sulphoxide (100 ml) was heated 18 h at 50° C. The solvent was evaporated under reduced pressure and the product precipitated by the addition of 10% sodium hydroxide solution. This solid was filtered off, washed with water and dried to give the same tosyl spiro nonane as that obtained in Example 1(ii).

(B) Step (ii) of Example 1 was repeated using powdered sodium hydroxide and a phase transfer catalyst in place of potassium tert.butoxide.

The dioxane obtained in Example 1(i) (3.02 g, 0.01 mol) dissolved in toluene (10 ml) was added dropwise with stirring to a mixture of p-toluenesulphonamide (1.71 g, 0.01 mol), powdered sodium hydroxide (1.4 g, 0.0.35 mol) potassium carbonate (1.4 g, 0.01 mol) and tetrabutylammonium bromide (0.322 g, 0.001 mol) in toluene (12 ml) kept at 50° C. After the addition was complete the mixture was stirred overnight at 120° C. After cooling the solid inorganic salt were filtered off and washed with toluene. The filtrate and washings were then shaken with water until neutral, dried and evaporated to leave a white solid. Recrystallisation from ethanol/water gave the same tosyl spiro nonane as that obtained in Example 1(ii).

EXAMPLE 9

Oxidation of N-tosyl-3,3-bishydroxymethyl azetidine (A) Preparation of N-Tosyl-3-hydroxymethyl azetidine-3-carboxylic acid.

Oxygen was bubbled rapidly through a stirred mixture of N-tosyl-3,3-bishydroxymethyl azetidine (0.5 g, 0.0018 mol), sodium bicarbonate (0.155 g, 0.0018 mol) and 5% Pt/C (0.3 g) in distilled water (10 ml) at 60° C. for 15 h. Sodium bicarbonate (0.155 g, 0.0018 mol) was added to maintain pH7-8 and the reaction continued a further 5 h. After cooling, the catalyst was filtered off, washed with water and the filtrate acidified with 4N HCl. Extraction with ether (x3), drying and evaporating left a white solid. The catalyst was washed again with water and the above procedure repeated to yield further solid. The whole was recrystallised from ethanol/water to give the title product as white crystals m.p. 148°–150° C.

(B) Preparation of N-Tosyl-3,3-dicarboxylazetidine.

Oxygen was bubbled rapidly through a stirred mixture of N-Tosyl-3,3-bishydroxymethyl azetidine (1.0 g, 0.0036 mol) sodium hydroxide (0.15 g, 0.0038 mol) and 5% Pt/C (0.6 g) in distilled water (20 ml) for 18 hrs at 50°–55° C. when the pH had fallen to 7–8. More sodium hydroxide (0.15 g, 0.0038 mol) was added and the mixture stirred another 6 hrs. Little change was observed and fresh catalyst (0.2 g) was added. After a further 12 hrs more catalyst (0.4 g) was added and the reaction continued until no further change was observed (37 h). A final fresh portion of catalyst (0.2 g) was added and the reaction mixture allowed to stir over the weekend (72 h) at 50° C. After cooling the catalyst was filtered off over "Celite" and the filtrate acidified with 4N HCl when an immediate white precipitate formed. This precipitate was filtered off, washed with water and dried to give a white solid. Extraction of the aqueous filtrate plus washings with ether followed by drying and evaporation gave further material. Recrystallisation of the combined solids from IPA/H₂O/EtOH gave the title product, m.p. 169° C.

EXAMPLE 10

Decarboxylation of N-tosyl-3,3-dicarboxyl azetidine

N-tosyl-3,3-dicarboxylazetidine (1 g) was warmed in an oil bath with 3 drops of pyridine. At an oilbath temperature of 140° C. CO₂ evolution and sintering started. After ½ h the oilbath temperature had reached 160° C., the evolution of CO₂ ceased and the contents were cooled down to room temperature. Addition of a few drops of HCl converted the glassy material into a white crystalline material, which was N-Tosyl-azetidine 3-carboxylic acid.

EXAMPLE 11

Integrated oxidation/decarboxylation

N-Tosyl-3,3-bishydroxymethyl azetidine (10 g, 0.037 mol) was suspended in distilled water (100 ml) and 30% NaOH (3 ml) added. Dioxane (50 ml) was then added in order to obtain a homogeneous solution, followed by 1 g of a 5% Pt/C catalyst. This mixture was heated under reflux with rapid stirring whilst a stream of oxygen was bubbled through at the rate of 600 ml.min$^{-1}$. The pH of the solution was maintained at 9–12 with 30% NaOH and the course of the oxidation followed by $^1$H nmr. After 24 h another 1 g of catalyst was added and after 48 h a further 2 g was added at which point all of the starting diol had been converted. In order to achieve conversion of any intermediates, a further 1 g catalyst was added after 120 h. After a total reaction time of 144 h, 5 g catalyst had been added and 10 ml 30% NaOH (0.074 mol). The solution was filtered whilst hot and the catalyst washed with dil NaOH and water. The filtrate and washings were then acidified with 4N HCl and extracted with ether (x3). The combined ether extracts were dried and evaporated to leave a white solid which, on recrystallisation from ethyl acetate, gave N-Tosyl azetidine 3-carboxylic acid.

EXAMPLE 12

Preparation of Azetidine 3-carboxylic acid

To crude N-Tosyl Azetidine 3-carboxylic acid (8.0 g, 0.314 mol) dissolved in liquid ammonia (175 ml) at −40° C. were added small pieces of sodium metal (3.82 g, 0.165 mol) until the blue colour persisted for 10 mins. Solid ammonium chloride (89 g) was then added giving a colourless solution. The ammonia was allowed to evaporate overnight under a stream of nitrogen and the residue dissolved in water. Acidification to pH3 with 4N HCl and extraction with ether (x4) removed neutral and acidic products. The aqueous layer was evaporated to dryness. This residue was dissolved in distilled water and purified by passage over Dowex 50W-X8 (H+) ion-exchange resin. The column was first eluted with water until neutral and the title product then recovered by eluting with 2N NH₄OH.

We claim:

1. Compounds of the formula

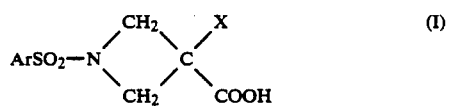
(I)

wherein Ar represents a para-tolyl group, and X represents a hydrogen atom, a carboxyl group or a hydroxymethyl group.

* * * * *